United States Patent
May

(10) Patent No.: US 7,166,843 B2
(45) Date of Patent: Jan. 23, 2007

(54) TECHNIQUE FOR DETECTING ETHYLENE OXIDE IN AIR

(75) Inventor: Randy Dean May, Glendora, CA (US)

(73) Assignee: SpectraSensors, Inc., San Diego, CA (US)

(*) Notice: Subject to any disclaimer, the term of this patent is extended or adjusted under 35 U.S.C. 154(b) by 325 days.

(21) Appl. No.: 10/766,327

(22) Filed: Jan. 29, 2004

(65) Prior Publication Data

US 2004/0245471 A1    Dec. 9, 2004

Related U.S. Application Data

(60) Provisional application No. 60/444,056, filed on Jan. 31, 2003.

(51) Int. Cl.
*G01N 21/35* (2006.01)

(52) U.S. Cl. .................................. 250/343

(58) Field of Classification Search ............ None
See application file for complete search history.

(56) References Cited

U.S. PATENT DOCUMENTS

| 5,257,256 A | 10/1993 | Terao et al. |
| 6,875,399 B1 * | 4/2005 | McVey .................. 422/3 |

* cited by examiner

*Primary Examiner*—Constantine Hannaher
(74) *Attorney, Agent, or Firm*—Fish & Richardson P.C.

(57) ABSTRACT

A system and method can detect ethylene oxide in a sample of gas, such as air. The system includes a light source operating at a wavelength where molecules typically found within air absorb light at a substantially lower level than ethylene oxide molecules. Exemplary wavelengths are in the range of approximately 1.6–2.2 µm, and in particular at 1.6 µm, 1.645 µm, 1.692 µm, 2.195 µm, 2.2 µm, 2.216 µm, passes through the sample of gas to be detected by a detector. In one variation, the light source is a tunable diode laser or a VCSEL and the ethylene oxide level is determined using harmonic spectroscopy.

20 Claims, 4 Drawing Sheets

TECHNIQUE FOR DETECTING ETHYLENE OXIDE IN AIR

This patent application claims the benefit of U.S. Patent Application Ser. No. 60/444,056, of Dr. Randy D. May, filed Jan. 31, 2003 which is hereby fully incorporated by reference.

BACKGROUND OF THE INVENTION

The present invention relates to a system and method for the detection of ethylene oxide in air. More specifically, the present invention relates to a technique for determining the level of ethylene in air present within one or more sample areas.

Ethylene Oxide is used in the production of solvents, antifreezes, textiles, detergents, adhesives, polyurethane foam, pharmaceuticals, fumigants, as well as sterilants for spices, cosmetics, and hospital equipment. While ethylene oxide is a necessary compound in the above applications, exposure to levels exceeding 0.5 ppm can be harmful both to individuals and to the environment. For example, studies have shown that in addition to side effects such as dizziness, nausea, and vomiting, ethylene oxide is linked to leukemia and other cancers. In addition, under certain circumstances, ethylene oxide contamination has been known to violently explode causing bodily injury and significant property damage. Accordingly, numerous types of monitors have been employed to determine the concentration of ethylene oxide in the workplace and other areas of interest.

Conventional techniques for measuring ethylene oxide in air rely primarily on the use of electrochemical sensors. These sensors operate by monitoring an electrical property, (e.g., the resistance, capacitance, dielectric, conductance, colorimetry, etc.) constant of a sensor element or solution in physical contact with a sample of air. The selected electrical property of the sensors change quantitatively as a function of the amount of ethylene oxide present in the sample gas and such changes are translated into ethylene oxide concentration measurements.

As the sensing elements in chemical sensors are necessarily exposed to gas samples, contaminants in the gas stream such as water, oils, and other airborne contaminants directly contact the sensors. While chemical sensors can, in some circumstances, provide reliable measurements for short periods of time after calibration, the exposure to the contaminants alter the electrical response of the sensor, thereby causing drifts in the calibration. This condition results in erroneous readings and can lead to eventual failure if the contaminants accumulate. Various filters (coalescing, adsorbents, and particle filters) have been employed to minimize the effects of foreign chemical/matter contamination, but historically these filtration schemes are only temporary solutions. This is due in part because the filters are easily saturated with contaminants or they leak and require replacement at irregular intervals.

Some conventional electrochemical sensors for the detection of ethylene oxide are configured to compensate for some types of contaminant that contacts the sensor head. For example, the EtOx ethylene oxide electrochemical sensor manufactured by MSA of Pittsburgh, Pa. adjusts ethylene oxide concentration measurements based on various concentrations of airborne contaminants as related to an equivalent of 1 ppm ethylene oxide including, 3079 ppm of hydrogen, 635 ppm of carbon monoxide, 0.8 ppm of isopropanol, and 0.2 ppm of formaldehyde. Electrochemical sensors are also prone to error from polar (heavy) molecules or ionic reactions on the sensor head. Accordingly, when calibrated, the baseline "zero" measurement for electrochemical sensors take into account the potential contaminants, and the "span" measurement is made by passing a known quantity of ethylene oxide in air through the electrochemical sensor and recording values of one or more of voltage, current, or conductance. Any change in the physical response of the electrochemical sensor head results in a change in the zero and span output levels and thus, the concentration detected by the sensor. While such sensors may provide accurate measurements for a limited period of time, they require frequent cleaning and replacement.

It should therefore be appreciated that there remains a need for a precise and durable technique for detection of ethylene oxide in air.

SUMMARY OF THE INVENTION

The current invention utilizes absorption spectroscopy, a well-known technique to measure the concentration of gases in air and other background gases. With such spectroscopic techniques, a light source is directed through a gas sample of interest onto a detector. The light source can be a conventional hot filament, a glow bar, a laser, or any suitable emitter in the wavelength region of interest. By monitoring the amount of light absorbed by the sample, at specific wavelengths, the concentration of the target gas can be determined accurately.

A common problem with absorption spectroscopy is interference among constituents in the gas sample being measured. This interference occurs when the gas of interest (in this case ethylene oxide) absorbs light at the same, or nearly the same, wavelength as another gas present in the sample. Air, which is composed of approximately 1–3% $H_2O$ and 365 ppmv $CO_2$ (along with N2 and O2 which do not absorb infrared light), typically has no ethylene oxide content.

The current invention operates in a wavelength range with minimal $H_2O$ and $CO_2$ absorption and preferably utilizes laser light sources for absorption spectroscopy, thereby minimizing the effects of interference due to the extremely high spectral purity of the laser (narrow line width). The current system incorporates a light source, such as those lasers used in automated, unattended, field instrumentation that operate at wavelengths between 1.6 and 2.7 microns ($\mu$m). The preferred laser is a VCSEL (vertical cavity surface emitting laser) or a tunable diode laser, such as that disclosed in U.S. Pat. No. 5,257,256, which is hereby fully incorporated by reference. TDLs are widely utilized in optical communications, laser printers, bar code readers, CD players, and laser pointers. Alternatively, a quantum cascade laser or a color center laser which operates in the 1–3 $\mu$m region may be utilized, but such lasers are not always suitable for use in commercial field instrumentation due to their relatively large physical size, high power consumption, high maintenance requirements (i.e., must often require cryogenically cooling), and cost.

The present system measures ethylene oxide at the absorption bands near 2.2 $\mu$m, and more specifically, at 2.195 $\mu$m, and 2.216 $\mu$m, where absorption by the infrared-absorbing constituents within air (with the two main constituents being water and carbon dioxide) are weak. FIGS. 1 and 3 illustrate transmission spectra (transmission=1−absorption) of ethylene oxide and $H_2O$ in the 2.2 $\mu$m region. As can be seen, there are several ethylene oxide absorption bands that can be used to monitor ethylene oxide in air. There are wavelengths in the air absorption spectrum, 2.195

μm, and 2.216 μm, where strong ethylene oxide bands exist, thereby allowing ethylene oxide concentration to be measured in air.

In some variations, the current invention uses harmonic spectroscopy, to improve detection sensitivity. Harmonic spectroscopy as used in the current system involves the modulation of the TDL laser or VCSEL wavelength at a high frequency (kHz-MHz) and detecting the signal at a multiple of the modulation frequency. In some embodiments, a 2216 nm DFB laser is used. If detection is performed at twice the modulation, the term second harmonic spectroscopy is used. Advantages are minimization of 1/f noise, removal of the sloping baseline that is present on transmission spectra (due to the fact that the laser output power increases as the laser injection current increases, and changing the laser injection current is how the laser is tuned), and detection against a zero background.

In one embodiment, the invention is disclosed in a system for detecting ethylene oxide in air. Such a system comprises a light source emitting light at a wavelength of approximately 2.2 microns, where the light source is positioned to emit light through a sample of air, a detector configured to detect the intensity of light emitted from the light source, and an electronics unit coupled to the detector for determining the level of ethylene oxide in the sample of air. The light source may be any light source that operates at or near the desired wavelength, and may include light sources such as tunable diode lasers, color center lasers, quantum cascade lasers, and VCSELs. Opposite the light source is a detector able to detect variations in light received thereby such as an InGaAs detector. In some variations, the light source emits light at a wavelength of approximately 2.22 microns, and in other variations the light source emits light at a wavelength of approximately 2.216 microns (via, for example, a 2216 nm DFB laser), and in yet other variations the light source emits light at a wavelength of approximately 2.195 microns. The electronics unit can translate the light level detected by the detector into a concentration of ethylene oxide within an air sample.

In another embodiment, the invention is provided in a system for detecting ethylene oxide in air comprising, a light source emitting light a wavelength of approximately 1.6 microns that is positioned to emit light through a sample of air, a detector (such as an InGaAs detector) configured to detect the intensity of light emitted from said light source, and an electronics unit coupled to said detector for determining the level of ethylene oxide in the sample of air. The light sources may be of any type that emits light at or near the desired wavelength, such as a tunable diode laser, a color center laser, a quantum cascade laser, and a VCSEL. This embodiment may also, in some variations, operate at a wavelength of approximately 1.69 microns, or in the alternative, in the wavelength range of approximately 1.64–1.65 microns or other suitable wavelengths where ethylene oxide absorbs light at a substantially greater level than the other major constituents of air (see FIG. 2).

The invention is also described in a method for determining the level of ethylene oxide within a sample of gas. Such a method comprises the steps of providing a light source emitting light at a wavelength where molecules within air (such as water and carbon dioxide) absorb light at a substantially lower level than ethylene oxide (see for example, FIGS. 1–3 for sample wavelengths), positioning a detector opposite the light source to detect the level of emitted light, supplying a sample of gas between the light source and the detector, and detecting the amount of light passing through the sample of gas. For example, the light may be emitted approximately at wavelengths such as 1.6 μm, 1.645 μm, 1.692 μm, 2.195 μm, 2.2 μm, and 2.216 μm.

In yet another embodiment of the invention, a system for detecting ethylene oxide in air is disclosed. The system includes a light source emitting light at a wavelength where air molecules absorb light at a substantially lower level than ethylene oxide that is positioned to emit light through a sample of air, a detector configured to detect the intensity of light emitted from the light source, and an electronics unit coupled to said detector for determining the level of ethylene oxide in the sample of air. The system may also include a plurality of sample areas (such as multiple sterilization rooms within a hospital), where each sample area contains air that may contain ethylene oxide. Each sample area is coupled to a sample area selector (by, for example, tubing or other ductwork) that may selectively deliver air from each sample areas to pass between the light source and the detector. This arrangement provides for a cost-effective technique that permits the use of a single ethylene oxide detector to detect levels of ethylene oxide within multiple sample areas.

The invention is also a method for determining the level of ethylene oxide in air, wherein the improvement comprises, using absorption spectroscopy in the wavelength range of approximately 2.2 μm.

A method for determining the level of ethylene oxide in air, wherein the improvement comprises, using absorption spectroscopy in the wavelength range of approximately 1.6 μm, is another embodiment of the invention.

A further embodiment of the invention is provided in a system for detecting ethylene oxide in a sample of gas comprising a Herriott cell having two opposing mirrors, a light source emitting light through the Herriott cell and configured to reflect off the mirrors to pass through the gas at least two times; a detector configured to detect the intensity of light emitted from the light source after the light reflects off the mirrors at least two times, and electronics coupled to said detector for determining the level of ethylene oxide in the gas. In some variations, the light source emits light approximately at a wavelength chosen from the group comprising: 1.6 μm, 1.645 μm, 1.692 μm, 2.195 μm, 2.2 μm, and 2.216 μm.

Though the current system is described in connection with the detection of ethylene oxide in air, it will be appreciated that the current system and method could be applied to other situations where it is desirable to measure ethylene oxide concentration in other gases.

DESCRIPTION OF THE PREFERRED EMBODIMENTS

The current system and method relate to the measurement of ethylene oxide in a gas, such as air, based on absorption of light at specific wavelengths where ethylene oxide molecules strongly absorb light. Generally, this technique is referred to as absorption spectroscopy, and is applicable to the measurement of a wide range of gases, liquids, and solids.

Figure 1:
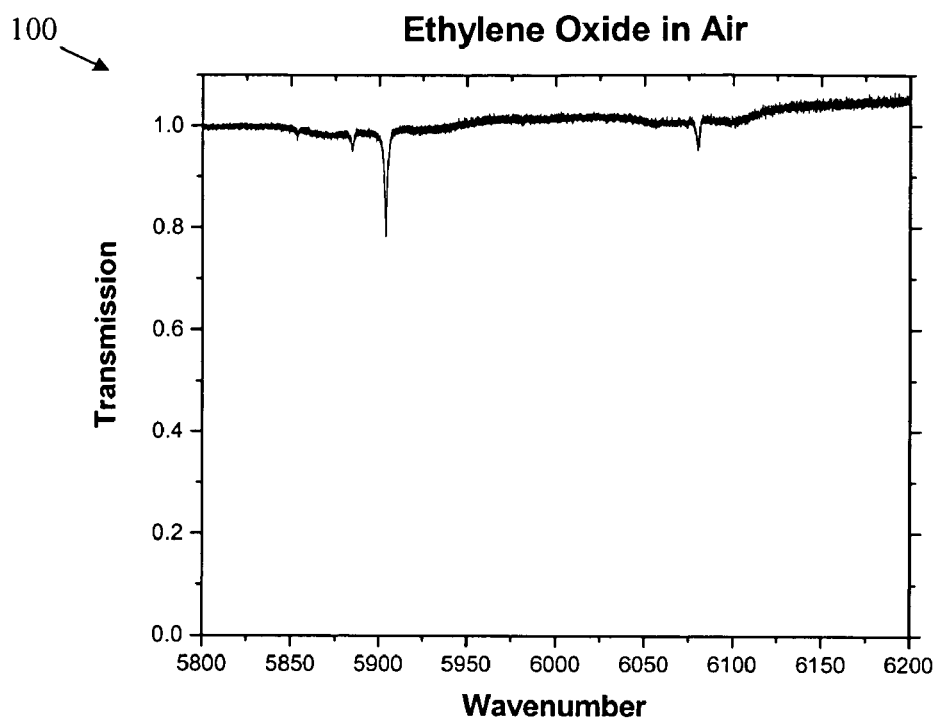
FIG. 1 is a transmission spectrum of ethylene oxide at wavenumbers ranging from 5800 to 6200.
Figure 2:
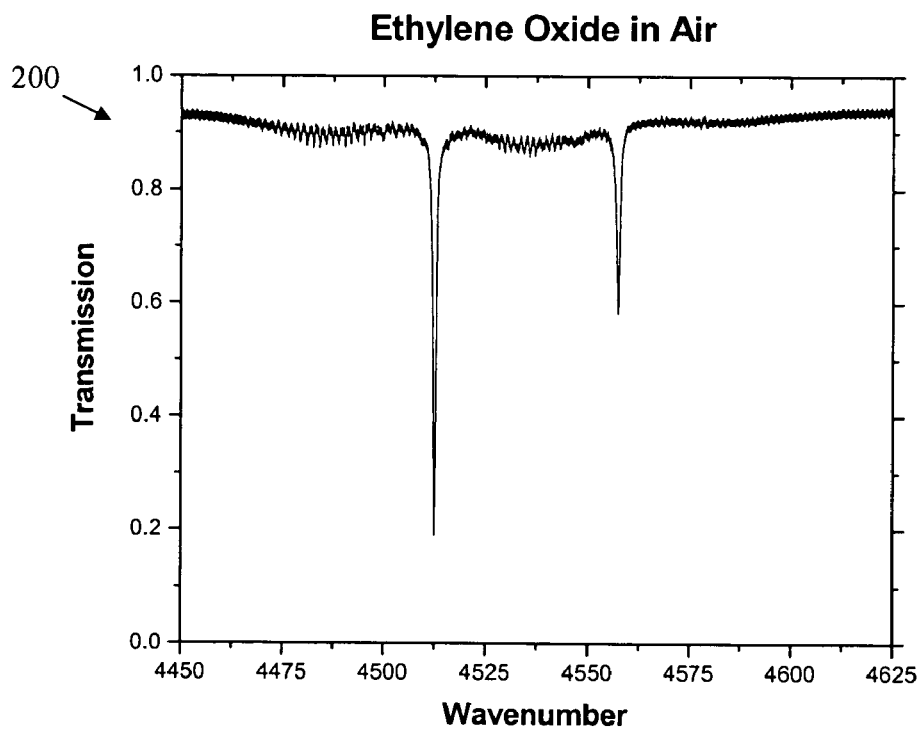
FIG. 2 is a transmission spectrum of ethylene oxide at wavenumbers ranging from 4450 to 4625.
Figure 3:
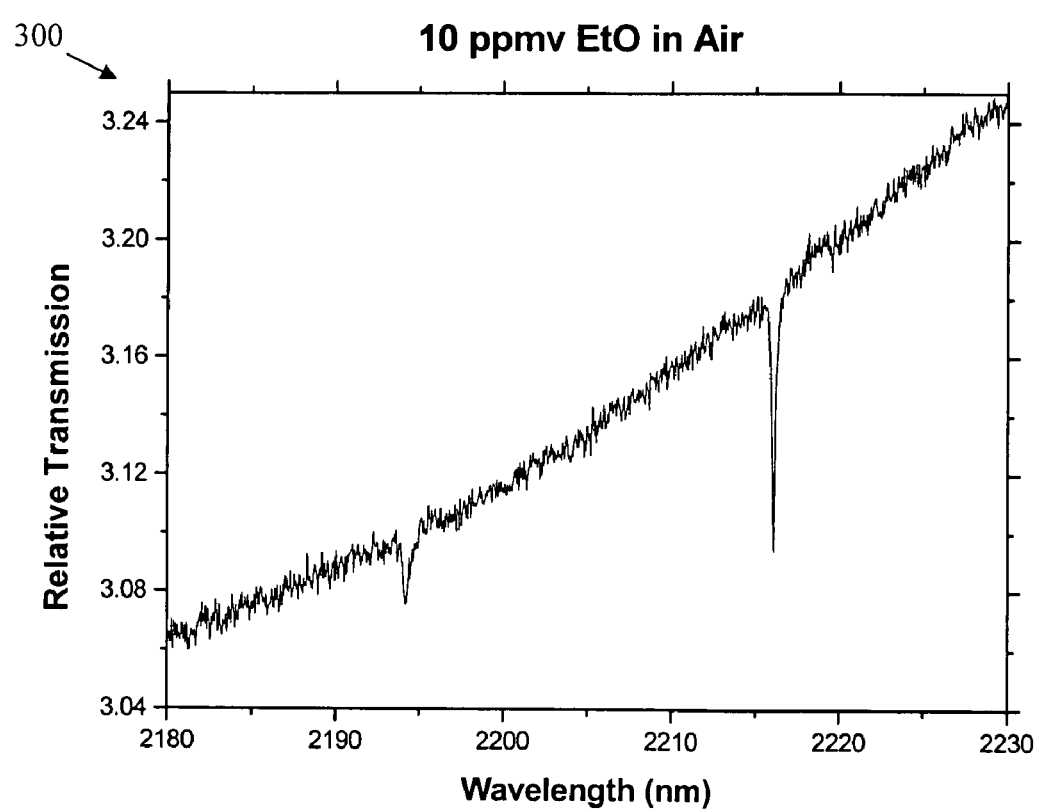
FIG. 3 is a transmission spectrum of ethylene oxide at wavelengths in the range of 2180 nm to 2230 nm for a sample of air containing 10 ppm ethylene oxide using a sensor having a 10 meter effective path length.
Figure 4:
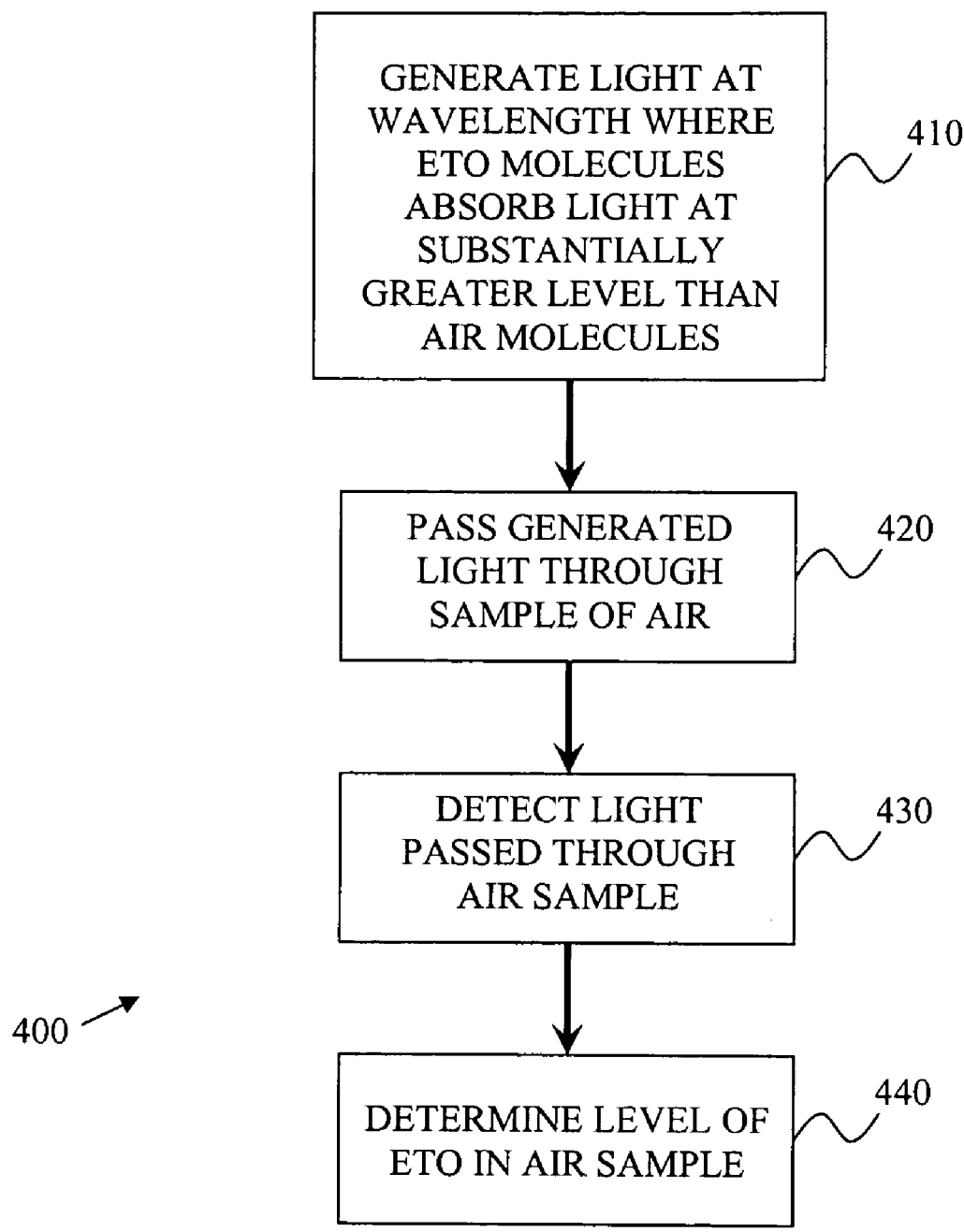
FIG. 4 is a process flow diagram according to a first embodiment of the invention.

With reference to FIG. 4, a method 400 for detecting ethylene oxide in air is provided. The method generates light at a wavelength where ethylene oxide molecules absorb light at a substantially greater level than other molecules typically found in air in relatively large volumes 410. This wavelength, for example, may be within the near infrared such as at 2.2 microns, and more preferably at 2.22 microns, 2.216 microns or 2.195 microns, or at 1.6 microns, 1.69 microns (and more specifically at 1.692 microns), or at 1.64–1.65 microns (and more specifically at 1.645 microns). A sample of air that may contain ethylene oxide is then passed by or between a light and a detector 420. The amount of light that passes through the air sample is then detected by a detector 430. Based on the detected amount of light, the level of ethylene oxide within the air sample may then be detected 440.

Figure 5:
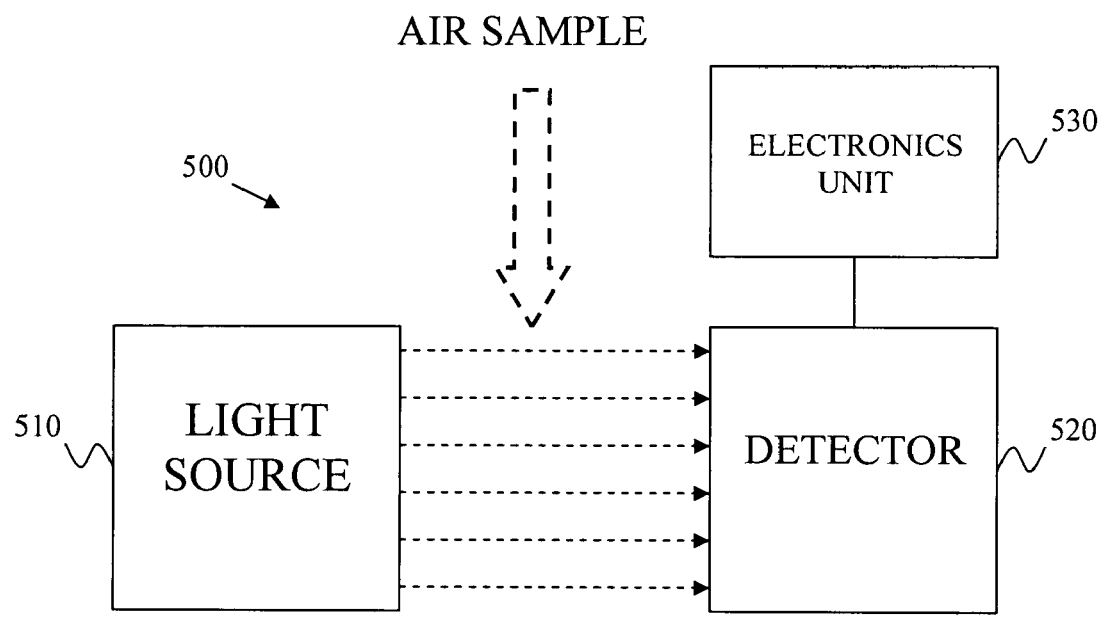
FIG. 5 is a schematic of an ethylene oxide detector.

FIG. 5 illustrates a system for detecting ethylene oxide in air 500. The system includes a light source 510 that is configured to emit light, a detector 520 positioned opposite the light emitting face of the light source 510, and an electronics unit 530 coupled to the detector for converting the light intensity detected by the detector into a corresponding volume or other measurement indicative of the amount of ethylene oxide within the air sample. Preferably, the laser light source is a VCSEL or a tunable diode laser configured to emit light in the 1.6–2.2 µm wavelength range, and more particularly, configured to operate at one of the following wavelengths: 1.645 µm, 1.695 µm, 2.195 µm, or 2.216 µm. For example, the light source may be a 2216 nm DFB laser. Alternatively, the light source may be a color center laser, a quantum cascade laser, or the like.

Depending on the desired sensitivity, the detector may directly detect light emitted from the light source 510, or the light may be reflected off opposing reflective surfaces (such as mirrors) to have a longer effective length. For example, the light source and detector may be housed within a Herriott cell having an effective length. Such a Herriott cell may comprise two opposing Pyrex gold coated mirrors, each preferable with a radius of curvature of 150 mm and a diameter of 25.4 mm. In this embodiment, the light source 510 is configured within the Herriott cell so that the emitted light bounces off each mirror approximately 30 times for a total distance of 4 meters. The light is then detected by the detector 520, which is coupled to the electronics unit 530 which contains software for converting the signals received into ethylene oxide concentration measurements. In some embodiments, the electronics unit 530 includes a 16-bit Motorola microcontroller to convert the signals received by the detector into parts per million by volume (ppmv). For calibration purposes, it is preferred that a control gas sample containing a known concentration of ethylene oxide is passed through the gas sensor prior to measurements.

It should also be recognized that depending on the application, the number of reflections of the Herriott cell may be adjusted. For example, if the ethylene oxide levels will be in the range of 0–100 ppmv, then the system as described above should be utilized. If the concentration level will be higher, 0–10,000 ppmv, then a single pass configuration may be used. In any configuration, it is important that the sufficient amount of air flows between the light source 510 and the detector 520. To further such air flow, the housing containing the light source 510 and the detector 520 may have an open cage or meshwork with sufficiently big openings so that air in an adjacent area may be sampled. Alternatively, air may be pumped through the system 500 (preferably at a constant flow rate) from one or more sample areas.

Figure 6:
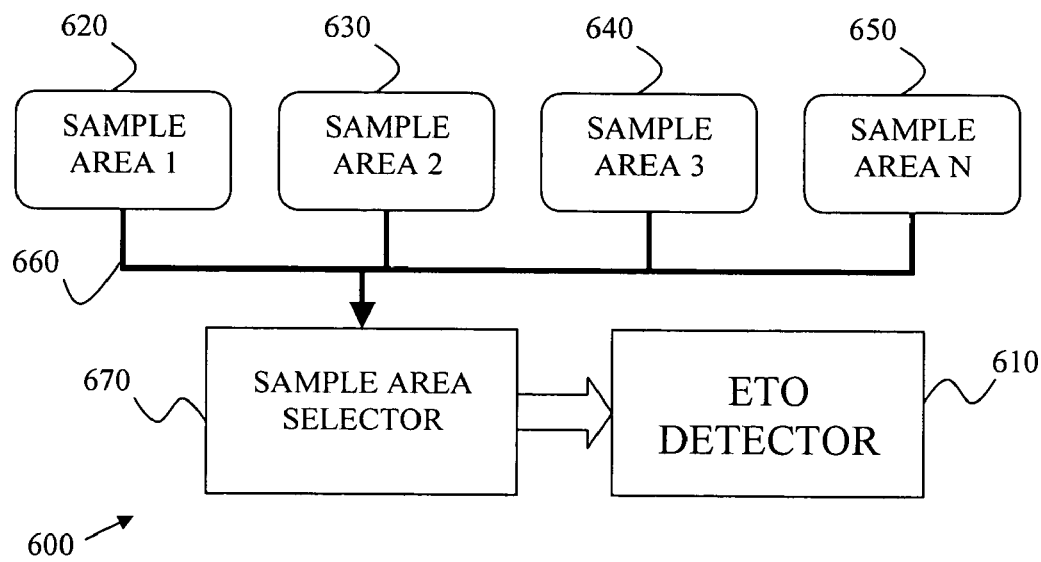
FIG. 6 is a schematic of an ethylene oxide detector for detecting the level of ethylene oxide within air from a plurality of sample areas.

With reference to FIG. 6, an ethylene oxide detection system is illustrated 600. The distributed detection system 600 includes an ethylene oxide detector 610 that is coupled to a plurality of sample areas 620, 630, 640 . . . 650, via connectors 660 that connect each sample area (via tubing ductwork, etc.) with a sample area selector 670 that selectively delivers samples of air from a desired sample area to the ethylene oxide detector 610. Such an arrangement may be particularly useful in a setting where there may be multiple sites that may contain ethylene oxide within air and only periodic (rather than continuous) measurements are needed. For example, a hospital may have multiple rooms that are used for sterilizing equipment. The ethylene oxide detector 610 would be able to test the air in each of the sterilization rooms to ensure that the ethylene oxide concentration is within safety standards. A user of the system 600 might select to sample a certain area via the sample selector 670 after a certain time period has expired that generally corresponds to a known amount of time needed for the ethylene oxide levels to drop below predetermined levels. Alternatively, the sample selector 670 may simply periodically analyze air samples from each of the sample areas 620, 630, 640 . . . 650 for a predetermined amount of time (e.g., two minutes for each sample area with one minute in between each sample area to purge any remnants of previous measurements).

It will, of course, be understood that modifications to the preferred embodiments will be apparent to those skilled in the art. For example, different techniques may be used for supplying gas samples between the light source and the detector and for converting the signals received by the detector into concentration measurements, and ethylene oxide may be detected in other background gases that do not have absorption lines at the wavelengths utilized herein. Consequently, the scope of the present invention should not be limited by the particular embodiments discussed above, but should be defined only by the claims set forth below and equivalents thereof.

What is claimed is:

1. A system for detecting ethylene oxide in air comprising:
    a light source emitting light having a width sufficiently narrow to conduct single line spectroscopy at a wavelength of approximately 2.2 microns, wherein said light source is positioned to emit light through a sample of air;
    a detector configured to detect the intensity of light emitted from said light source; and
    an electronics unit coupled to said detector for determining the level of ethylene oxide in the sample of air.

2. The system of claim 1, wherein said light source is chosen from the group comprising: a tunable diode laser, a color center laser, a quantum cascade laser, and a VCSEL.

3. The system of claim 1, wherein said detector is an InGaAs detector.

4. The system of claim 1, wherein said light source emits light at a wavelength of approximately 2.22 microns.

5. The system of claim 1, wherein said light source emits light at a wavelength of approximately 2.216 microns.

6. The system of claim 1, wherein said light source emits light at a wavelength of approximately 2.195 microns.

7. A system for detecting ethylene oxide in air comprising:
a light source emitting light having a width sufficiently narrow to conduct single line spectroscopy at a wavelength of approximately 1.6 microns, wherein said light source is positioned to emit light through a sample of air;
a detector configured to detect the intensity of light emitted from said light source; and
an electronics unit coupled to said detector for determining the level of ethylene oxide in the sample of air.

8. The system of claim 7, wherein said light source is chosen from the group comprising: a tunable diode laser, a color center laser, a quantum cascade laser, and a VCSEL.

9. The system of claim 7, wherein said detector is an InGaAs detector.

10. The system of claim 7, wherein said light source emits light at a wavelength of approximately 1.69 microns.

11. The system of claim 7, wherein said light source emits light at a wavelength in the range of approximately 1.64–1.65 microns.

12. A method for determining the level of ethylene oxide in a sample of gas comprising the following steps:
providing a light source emitting light having a width sufficiently narrow to conduct single line spectroscopy at a wavelength chosen from the group comprising 1.6 µm, 1.645 µm, 1.692 µm, 2.195 µm, 2.2 µm, and 2.216 µm;
positioning a detector opposite the light source to detect the level of emitted light; supplying a sample of gas between the light source and the detector; and detecting the amount of light passing through the sample of gas.

13. A system for detecting ethylene oxide in air comprising:
a light source emitting light having a width sufficiently narrow to conduct single line spectroscopy at a wavelength where ethylene oxide molecules absorb light at a substantially greater level than other molecules within air, wherein said light source is positioned to emit light through a sample of air;
a detector configured to detect the intensity of light emitted from said light source; and
an electronics unit coupled to said detector for determining the level of ethylene oxide in the sample of air.

14. The system of claim 13, further comprising: a plurality of sample areas, each sample area containing air that may contain ethylene oxide; and a sample area selector, for selectively delivering air from said plurality of sample areas to pass between said light source and said detector.

15. A system for detecting ethylene oxide in a sample of gas comprising:
a Herriott cell having two opposing mirrors;
a light source emitting light through said Herriott cell and configured to reflect off the mirrors to pass through the gas at least two times;
a detector configured to detect the intensity of light emitted from said light source after the light reflects off the mirrors at least two times; and
electronics coupled to said detector for determining the level of ethylene oxide in the gas; and
wherein said light source emits light having a width sufficiently narrow to conduct single line spectroscopy approximately at a wavelength chosen from the group comprising: 1.6 µm, 1.645 µm, 1.692 µm, 2.195 µm, 2.2 µm, and 2.216 µm.

16. An apparatus comprising:
means for emitting light at a wavelength having a width sufficiently narrow to conduct single line spectroscopy at a wavelength corresponding to an ethylene oxide absorption line;
means for detecting a level of emitted light; and
means for supplying a sample of gas between the means for emitting light and the means for detecting a level of emitted light.

17. An apparatus as in claim 16, wherein emitted light is at a wavelength chosen from a group comprising 1.6 µm, 1.645 µm, 1.692 µm, 2.195 µm, 2.2 µm, and 2.216 µm.

18. An apparatus comprising:
means for emitting light having a width sufficiently narrow to conduct single line spectroscopy at a wavelength where ethylene oxide molecules absorb light at a substantially greater level than other molecules within a sample of air;
a detector configured to detect the intensity of light emitted from said means for emitting light; and
an electronics unit coupled to said detector for determining the level of ethylene oxide in the sample of air.

19. An apparatus as in claim 18, wherein emitted light is at a wavelength chosen from a group comprising 1.6 µm, 1.645 µm, 1.692 µm, 2.195 µm, 2.2 µm, and 2.216 µm.

20. An apparatus as in claim 18, wherein said means for emitting light is chosen from a group comprising: a tunable diode laser, a color center laser, a quantum cascade laser, and a VCSEL.

* * * * *